(12) United States Patent
Hashino et al.

(10) Patent No.: US 9,132,045 B2
(45) Date of Patent: Sep. 15, 2015

(54) ABSORBENT ARTICLE

(75) Inventors: Akira Hashino, Kagawa (JP); Yuki Noda, Kagawa (JP); Shinpei Komatsu, Kagawa (JP)

(73) Assignee: Unicharm Corporation, Ehime (JP)

(*) Notice: Subject to any disclaimer, the term of this patent is extended or adjusted under 35 U.S.C. 154(b) by 342 days.

(21) Appl. No.: 13/813,476

(22) PCT Filed: Aug. 1, 2011

(86) PCT No.: PCT/JP2011/067613
§ 371 (c)(1),
(2), (4) Date: Apr. 9, 2013

(87) PCT Pub. No.: WO2012/017991
PCT Pub. Date: Feb. 9, 2012

(65) Prior Publication Data
US 2013/0211360 A1 Aug. 15, 2013

(30) Foreign Application Priority Data

Aug. 2, 2010 (JP) ................... 2010-174040

(51) Int. Cl.
*A61F 13/15* (2006.01)
*A61F 13/475* (2006.01)
*A61F 13/511* (2006.01)
*A61F 13/533* (2006.01)
*A61F 13/536* (2006.01)
*A61F 13/51* (2006.01)

(52) U.S. Cl.
CPC ....... *A61F 13/4756* (2013.01); *A61F 13/15699* (2013.01); *A61F 13/15707* (2013.01); *A61F 13/51104* (2013.01); *A61F 13/51108* (2013.01); *A61F 13/533* (2013.01); *A61F 13/536* (2013.01); *A61F 2013/51078* (2013.01)

(58) Field of Classification Search
CPC ........... A61F 13/4756; A61F 13/51104; A61F 13/51108; A61F 13/533; A61F 13/536; A61F 2013/51078; A61F 2013/5108; A61F 2013/51083; A61F 2013/51085
USPC .......................................... 604/380, 385.101
See application file for complete search history.

(56) References Cited

U.S. PATENT DOCUMENTS

| | | | | |
|---|---|---|---|---|
| 5,925,026 A | * | 7/1999 | Arteman et al. | 604/383 |
| 2006/0276767 A1 | * | 12/2006 | Ueminami et al. | 604/385.31 |
| 2013/0226123 A1 | * | 8/2013 | Kudo et al. | 604/380 |

FOREIGN PATENT DOCUMENTS

| EP | 2 151 220 A1 | 2/2010 |
|---|---|---|
| JP | 2003-033397 A | 2/2003 |
| JP | 2004-298281 A | 10/2004 |
| JP | 2010-142367 A | 7/2010 |
| WO | WO 2008/129138 A1 | 10/2008 |
| WO | WO 2010/074339 A1 | 7/2010 |

OTHER PUBLICATIONS

Japanese Office Action and English translation from corresponding Japanese application No. 2010-174040 dated Aug. 6, 2014 (4 pgs).
International Search Report from corresponding PCT application No. PCT/JP2011067613 dated Oct. 11, 2011 (3 pgs).
Chinese First Office Action and English translation from corresponding Chinese application No. 201180037905.0 dated Apr. 3, 2014 (10 pgs).
European extended Search Report from corresponding European application No. 11814616.6 dated Apr. 8, 2014 (5 pgs).

* cited by examiner

*Primary Examiner* — Lynne Anderson
(74) *Attorney, Agent, or Firm* — Brinks Gilson & Lione

(57) ABSTRACT

An absorbent article in which a plurality of first compressing units are provided spaced apart on both-side edges of a region corresponding to an excretion unit in an absorber, and a plurality of second compressing units are provided spaced apart over the entire region in the absorber 10 excluding the region 11 in which the first compressing units 12 are provided. The dimensions along the longitudinal direction of the absorbent article in the plan view shape of the first compressing units are configured so as to be longer than the dimensions along the width direction of the absorbent article, and the dimensions along the width direction of the absorbent article in the plan view shape of the second compressing units are configured so as to be longer than the dimensions along the longitudinal direction of the absorbent article.

16 Claims, 7 Drawing Sheets

ABSORBENT ARTICLE

RELATED APPLICATION

Figure 1:
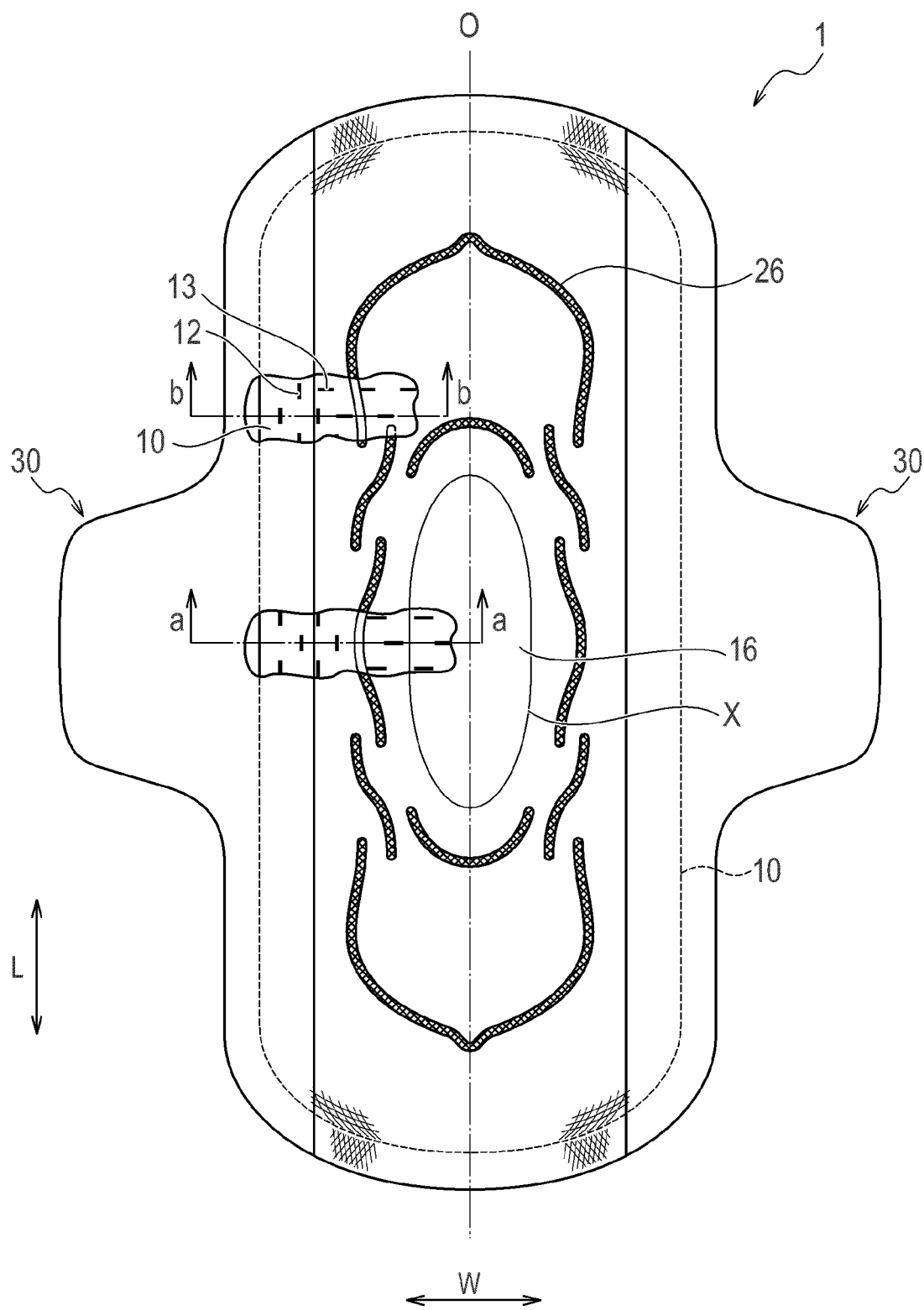

This application is a 35 U.S.C. §371 national phase filing of International Patent Application No. PCT/JP2011/067613 filed Aug. 1, 2011, to which priority is claimed under 35 U.S.C. §120 and through which priority is claimed under 35U.S.C. §119 to Japanese Patent Application No. 2010-174040, filed Aug. 2, 2010.

TECHNICAL FIELD

The present invention relates to an absorbent article.

BACKGROUND ART

Conventional absorbent articles are known as having an absorber provided with a plurality of compressing units spaced apart (for example, see Patent Document 1).

RELATED ART DOCUMENT

Patent Document

[Patent Document 1] Japanese Unexamined Patent Application Publication No. 2003-33397

SUMMARY OF INVENTION

Problems to be Solved by Invention

However, the applicant discovered the following problems in the absorber articles described above.

The absorbent article illustrated in Patent Document 1 is problematic in that, because no compressing unit is provided on the region of the absorber corresponding to the excretion unit, the region corresponding to the excretion unit is thicker than the peripheral region of the region corresponding to the excretion unit, and therefore the absorbent article tends to fit too snugly to the wearer's body around the excretion unit, and may give the wearer the sensation of a foreign body.

The absorbent article illustrated in Patent Document 1 is also problematic in that, because no compressing unit is provided on the region of the absorber corresponding to the excretion unit, the region corresponding to the excretion unit is less rigid than the region in the peripheral region of the region corresponding to the excretion unit, which is provided with compressing units, and therefore, when worn, the region corresponding to the excretion unit is liable to get twisted when an external force from the wearer's inner thigh is added, preventing a fit to the wearer's body around the excretion unit and giving rise to the risk of fluid leakage occurring.

The absorbent article illustrated in Patent Document 1 is further problematic in that, because the above-described compressing units do not have a linear shape in a plan view shape, it is not possible to direct the stiffness of the absorber, and therefore when an external force from the width direction of the absorbent article is added by the wearer's actions such as walking, the absorber is liable to get twisted and there is a risk that fluid leakage will occur.

Therefore, the present invention has been achieved in view of the above problems and an object thereof is to provide an absorbent article in which it is possible to maintain flexibility and prevent twisting while providing a product that is entirely thin Means for Solving the Problems A first characteristic of the present invention is an absorbent article comprising: a liquid-permeable topsheet; a liquid-impermeable backsheet; and an absorber disposed between the topsheet and the backsheet, wherein a plurality of first compressing units are provided spaced apart on both-side edges of the region corresponding to the excretion unit in the absorber, a plurality of second compressing units are provided spaced apart over the entire region in the absorber excluding the region in which the first compressing units are provided, the dimensions along the longitudinal direction of the absorbent article in the plan view shape of the first compressing units are configured so as to be longer than the dimensions along the width direction of the absorbent article, and the dimensions along the width direction of the absorbent article in the plan view shape of the second compressing units are configured so as to be longer than the dimensions along the longitudinal direction of the absorbent article.

ADVANTAGEOUS EFFECTS OF INVENTION

[FIG. 1] It is a plan view in which an absorbent article according to a first embodiment of the present invention is seen from a skin contact surface side.

Figure 2:
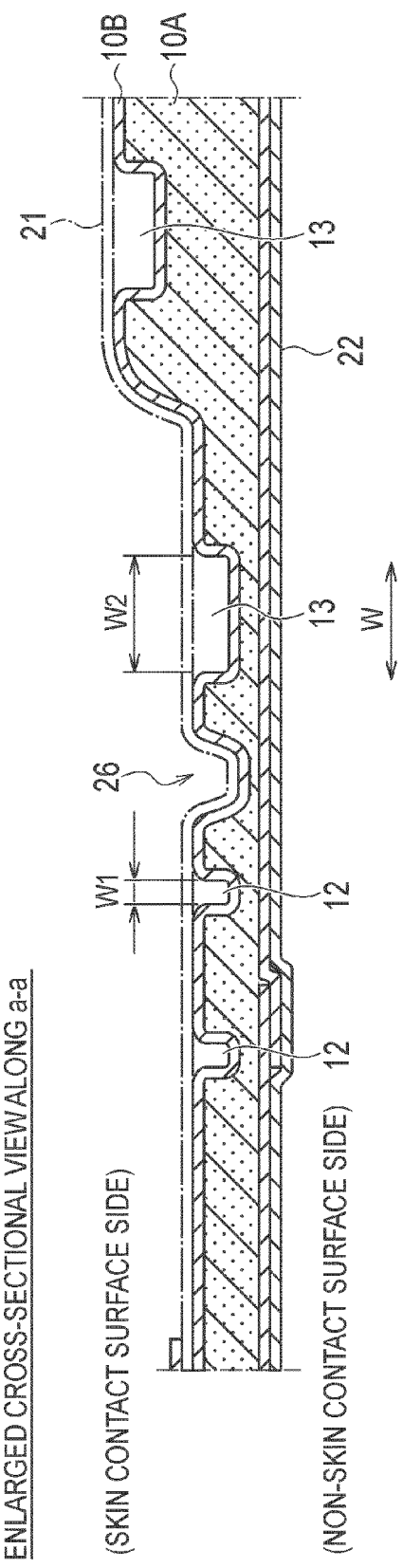
Figure 2:
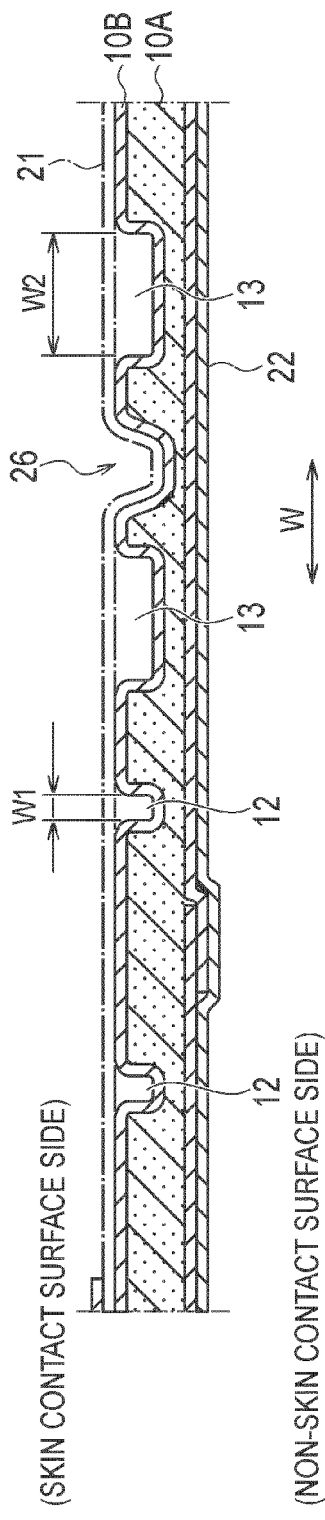

[FIG. 2] It is a cross-sectional view along line a-a and a cross-sectional view along line b-b in a plan view in which the absorbent article according to the first embodiment of the present invention is seen from the skin contact surface side.

Figure 3:
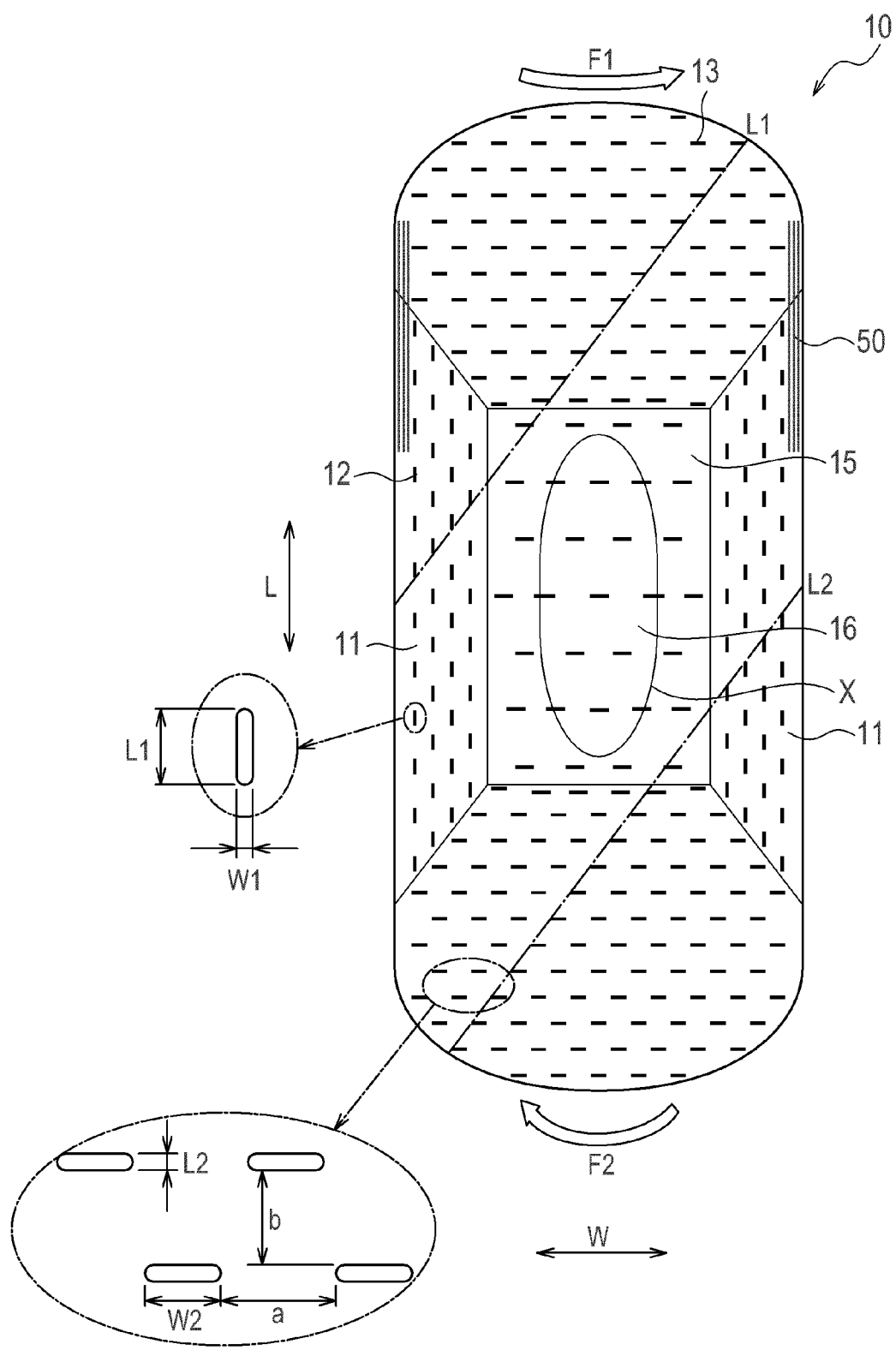

[FIG. 3] It is a plan view in which an absorber of the absorbent article according to the first embodiment of the present invention is seen from a skin contact surface side.

Figure 4:
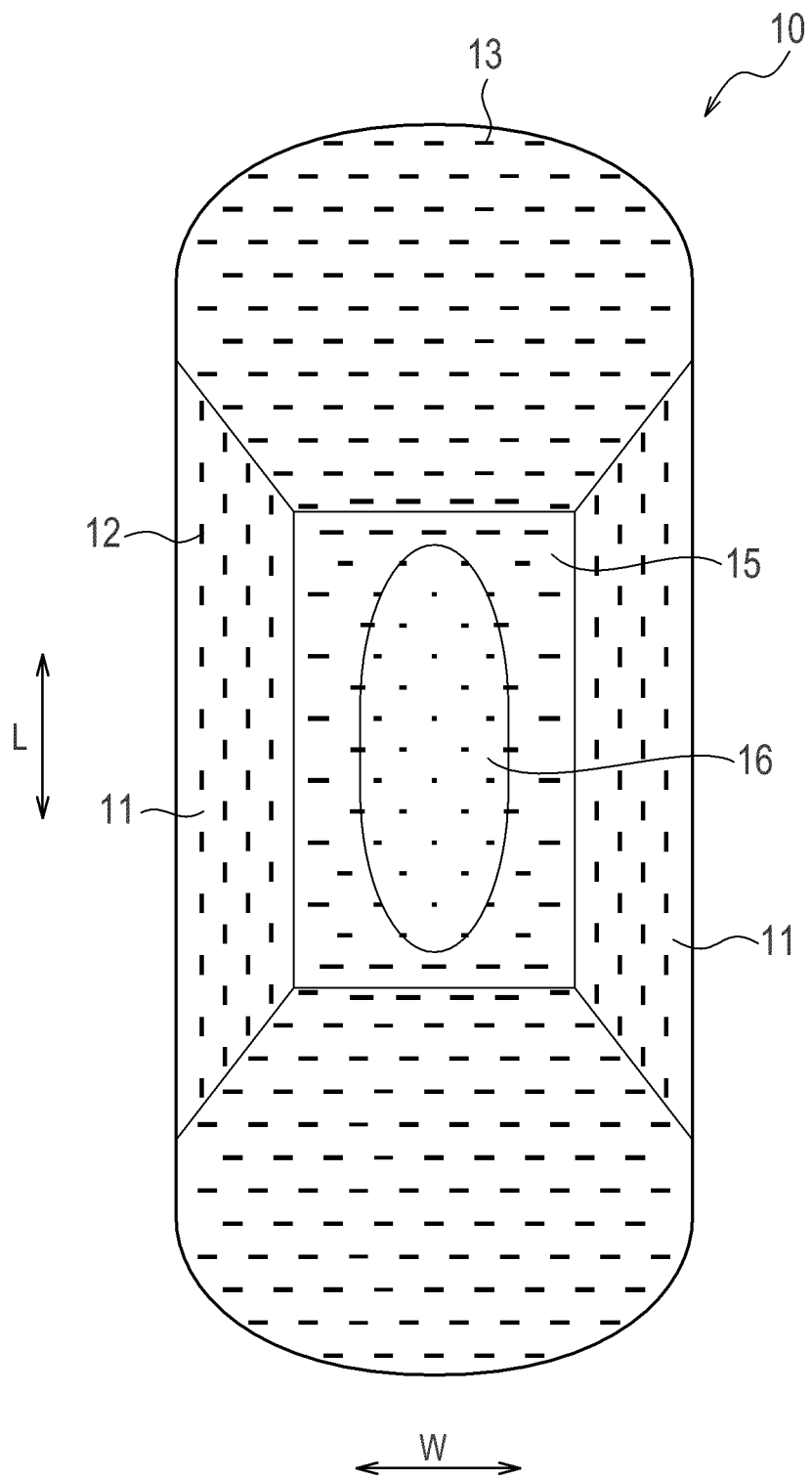

[FIG. 4] It is a plan view in which an absorber of the absorbent article according to the first embodiment of the present invention is seen from a skin contact surface side.

Figure 5:
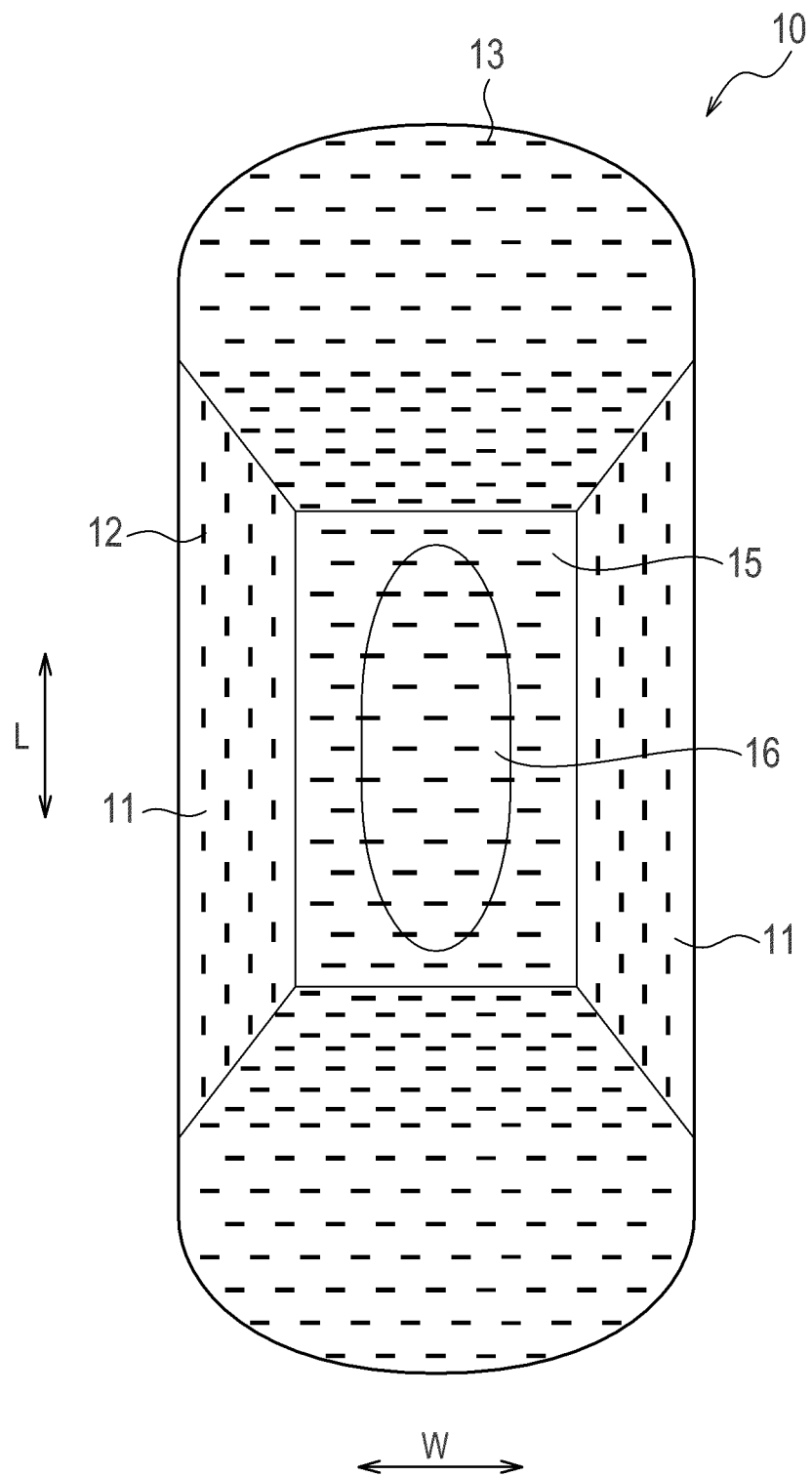

[FIG. 5] It is a plan view in which an absorber of the absorbent article according to the first embodiment of the present invention is seen from a skin contact surface side.

Figure 6:
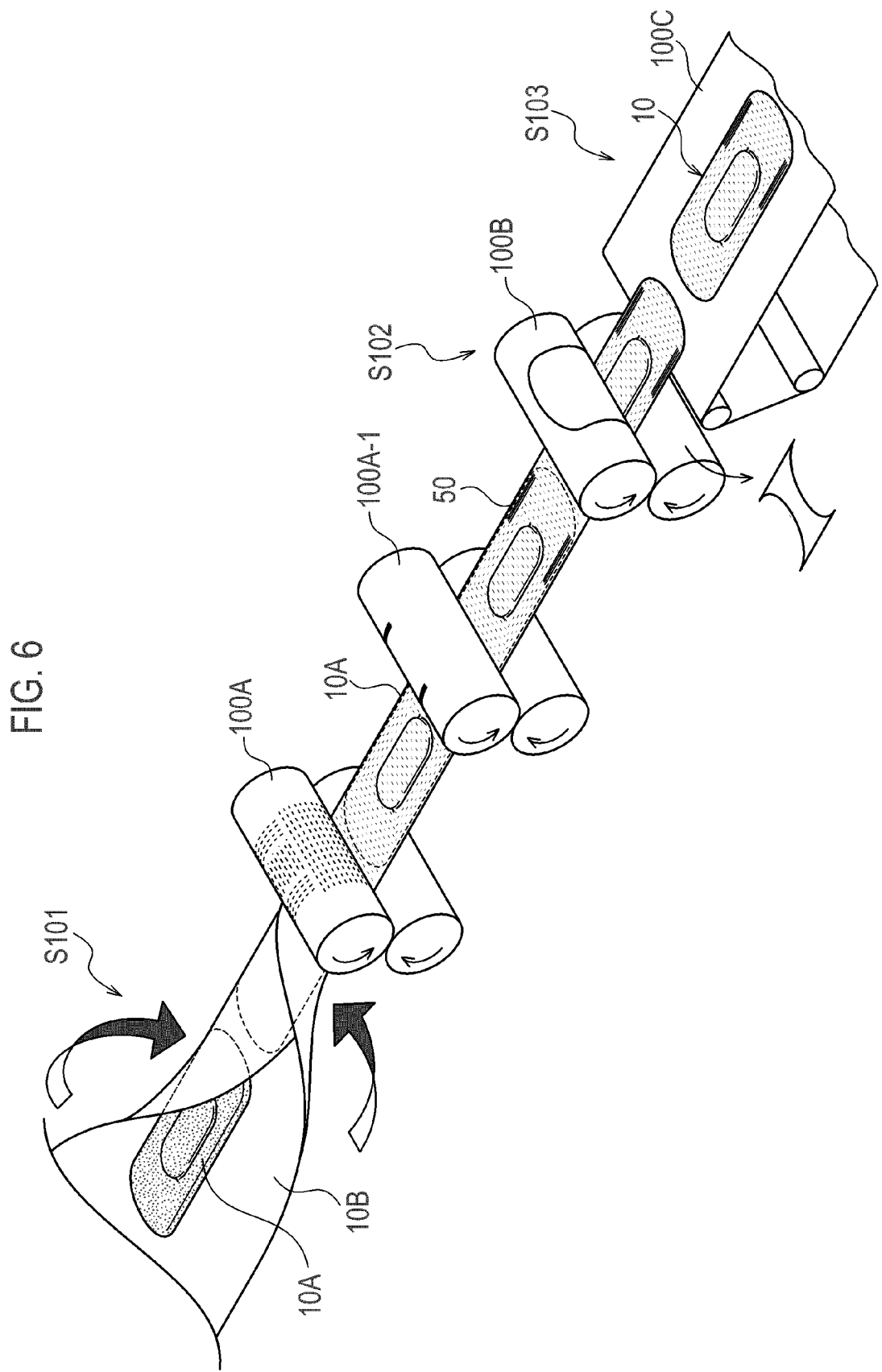

[FIG. 6] It is a diagram explaining a method of manufacturing the absorbent article according to the first embodiment of the present invention.

Figure 7:
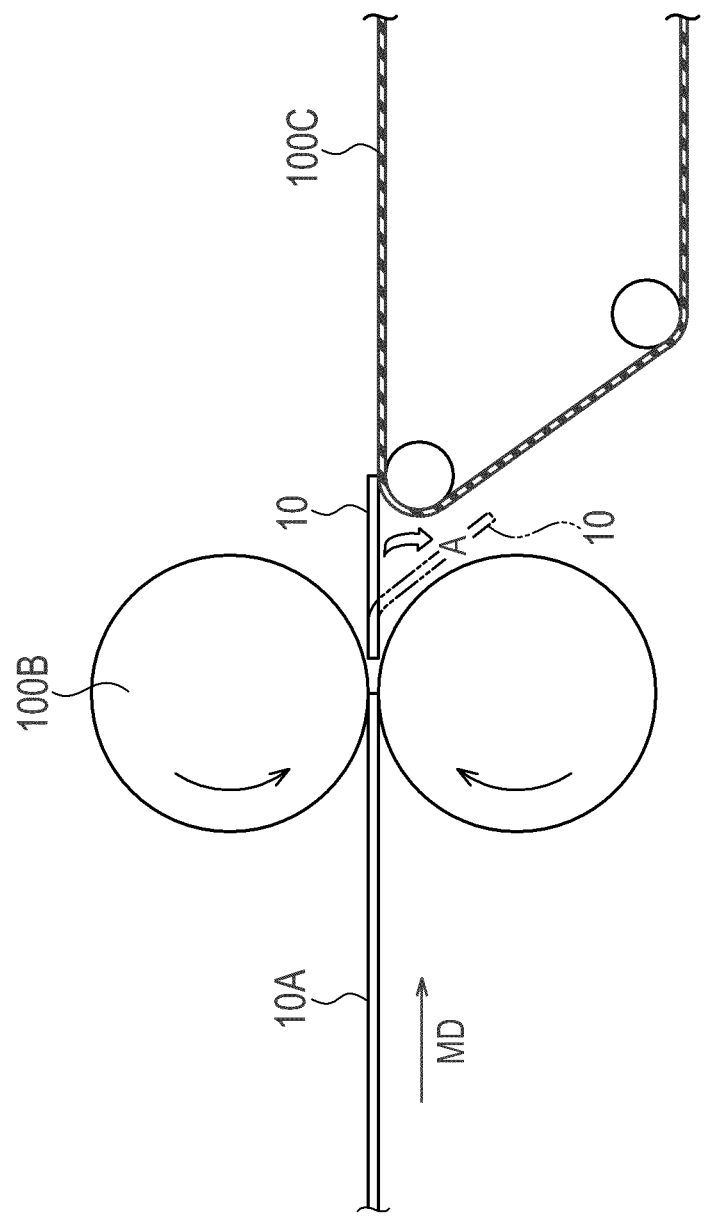

[FIG. 7] It is a diagram explaining a method of manufacturing the absorbent article according to the first embodiment of the present invention.

DESCRIPTION OF EMBODIMENTS (First Embodiment of the Present Invention)

With reference to FIG. 1 to FIG. 7, an absorbent article 1 according to a first embodiment of the present invention will be described. The absorbent article 1 according to this embodiment may be, for example, a paper diaper, an incontinence pad, or a sanitary napkin.

As illustrated in FIG. 1, the absorbent article 1 according to this embodiment may have a pair of wing units 30 formed so as to both extend in an outward width direction W. The absorbent article 1 according to this embodiment may also have a pair of rear wing units (not illustrated) in the rear of the wing units 30 in the longitudinal direction L.

Also, as illustrated in FIG. 1 and FIG. 2, the absorbent article 1 according to this embodiment may be provided with a plurality of compression grooves 26 configured so as to compress from the topsheet 21 to the absorber 10 along the longitudinal direction L.

As illustrated in FIG. 2, the absorbent article 1 according to this embodiment has a liquid-permeable topsheet 21, a liquid-impermeable backsheet 22, a sidesheet 31 which configures the wing units 30, and an absorber 10 arranged between the topsheet 21 and the backsheet 22. The absorbent article 1 according to this embodiment may also have a second sheet between the topsheet 21 and the absorber 10.

The absorber 10 is configured by an absorber core 10A made up of ground pulp and superabsorbent polymer, and a core wrap 10B which wraps up the absorber core 10A. In this case, this superabsorbent polymer is a granular polymer of sodium acrylate copolymer.

The core wrap 10B is a sheet made of any material that absorbs liquid. For example, tissue may be used as the core wrap, or an air-laid sheet made by air-laying hydrophilic fibers and ground pulp into a sheet shape may be used.

Herein, as illustrated in FIG. 1 and FIG. 2, the interior of the region 15 corresponding to the excretion unit may be provided with a region 16 configured such that the weight per unit area of the absorber is higher than in the peripheral region.

For example, the weight per unit area of the absorber 10 in the region 16 may be 300 $g/m^2$ and the thickness of the absorber 10 in the region 16 may be 3 mm, whereas the weight per unit area of the absorber 10 in the peripheral region of the region 16 may be 100 $g/m^2$ and the thickness of the absorber 10 in the peripheral region of the region 16 may be 2 mm.

The stiffness of the absorber 10 is preferably within the range of 2 mN to 3 mN. It is noted that the stiffness is a value measured by using the Gurley method specified in JIS-1096 (updated in 1994).

For the topsheet 21, a through-air nonwoven cloth made up of a polyolefin fiber such as polyethylene, polypropylene or polyethylene terephthalate, or an open-pored polyethylene film may be used.

For the backsheet 22, a polyolefin film may be used, and for the sidesheet 31, a spun-bond or through-air nonwoven cloth made up of a polyolefin fiber such as polyethylene, polypropylene or polyethylene terephthalate may be used.

Further, for the second sheet, a through-air nonwoven cloth made up of a polyolefin fiber such as polyethylene, polypropylene or polyethylene terephthalate may be used.

The absorbent article 1 according to this embodiment may also be provided with a leakage-preventing wall (not illustrated) along the longitudinal direction L.

Herein the leakage-preventing wall may be configured by arranging a stretched filiform elastic member into a base nonwoven cloth such spun-bond or SMS, made up of a polyolefin fiber such as polyethylene, polypropylene or polyethylene terephthalate.

As illustrated in FIG. 3, both-side edges of the region 15 corresponding to the excretion unit in the absorber 10 are provided with a plurality of first compressing units 12 which are spaced apart. Herein the plurality of first compressing units 12 may be arranged not only to be spaced apart along the width direction W of the absorbent article 1, but also to be spaced apart along the longitudinal direction L of the absorbent article 1.

It is noted that the region 15 corresponding to the excretion unit is the region contacted to the wearer's vaginal opening, and when, for example, the absorbent article 1 is worn on the wearer's underwear, it is the region arranged between the two leg holes of the underwear.

Herein, when the wearer wears the absorbent article 1 on the underwear, the absorbent article 1 is secured onto the underwear by rolling up the wing units 30 onto the crotch of the underwear and unfolding the rear wing units on top of the underwear.

Therefore, when, for example, the wing units 30 are provided in the absorbent article 1 according to this embodiment, then the center line of the above-described region 15 corresponding to the excretion unit matches the center line of the wing units 30 in the longitudinal direction L.

When no wing units 30 are provided and the length dimension along the width direction W of the absorbent article 1 is almost constant, then the center line of the above-described region 15 corresponding to the excretion unit is the line stretching in the width direction W in the center of the longitudinal direction L of the absorbent article 1 (that is, the product).

Also, in the case wherein no wing units 30 are provided, then when the wearer wears the absorbent article 1 on the underwear, the absorbent article 1 may be secured onto the underwear by matching the position at which the length dimension of the width direction W of the absorbent article 1 is shortest to the crotch of the underwear. In such a case, namely, in the case where no wing units 30 are provided in the absorbent article 1 according to this embodiment, then the center line of the above-described region 15 corresponding to the excretion unit is the line stretching in the width direction W at the point at which the length dimension of the width direction W of the absorbent article 1 is shortest.

For example, in a case where the dimensions of the longitudinal direction of the absorbent article 1 (the product length) is "21 cm," then the region 15 corresponding to the excretion unit is arranged at a position "40 mm" to "55 mm" from the front end and rear end of the longitudinal direction L of the absorber 10, and is arranged at a position "6 mm" to "16 mm" from both ends of the width direction W of the absorber 10. Also, in a case where the dimensions of the longitudinal direction of the absorbent article 1 (the product length) are other dimensions, then the position at which the region 15 corresponding to the excretion unit is arranged becomes a different position.

Herein, the plan view shape of the first compressing units 12 is configured such that, as illustrated in FIG. 3, the dimension L1 along the longitudinal direction L of the absorbent article 1 is longer than the dimension W1 along the width direction W of the absorbent article 1.

For example, in terms of the stiffness of the absorber 10, the dimension L1 is preferably 3 mm or less, and the dimension W1 is preferably 2 mm or less.

Further, in the absorbent article 1 according to this embodiment, as illustrated in FIG. 3, the plurality of first compressing units 12 are provided in a region 11 on both-side edges of the region 15 corresponding to the excretion unit. The region 11 may be a trapezoid as illustrated in FIG. 3, but it may also be any other shape.

Also, the plurality of first compressing units 12 are in a shape that comprises a straight line along the longitudinal direction L of the absorbent article 1. In this embodiment, in the plurality of first compressing units 12, both tips of the longitudinal direction L of the absorbent article 1 are formed in a semicircular shape. In addition, the plurality of first compressing units 12 may have the same area and shape, or may have different areas and shapes.

According to such a configuration, because the first compressing units 12 are provided spaced apart along the width direction W of the absorbent article 1, high-stiffness units (the first compressing units 12) and low-stiffness units (excluding the first compressing units 12) are alternately repeated, resulting in the presence of a plurality of creases.

As a result, when an external force from the width direction W of the absorbent article 1 is applied to the absorbent article 1, that is, when an external force from the wearer's inner thighs is applied, then the absorbent article 1 is liable to be bent along the longitudinal direction L of the absorbent article 1 in the region 11 that is both-side edges of the region 15 corresponding to the excretion unit. Accordingly, even when the wearer closes the thighs, it is possible to combine a reduction in discomfort (hardness) for the wearer with an improvement in the fit and so on.

Moreover, according to such a configuration, because the plurality of first compressing units 12 are provided spaced apart along the longitudinal direction L of the absorbent article 1 and because the plurality of first compressing units 12 are in a shape that comprises a straight line along the longitudinal direction L of the absorbent article 1, even when menstrual blood flows in the width direction W of the absorbent article 1, the menstrual blood can be diffusion-inducted in the longitudinal direction L of the absorbent 1 and side leakage of the menstrual blood can be prevented by means of the first compressing units 12.

In particular, even when the absorbent article 1 is repeatedly deformed, the topsheet 21 and the like are not prone to be torn, because in the plurality of first compressing units 12, both tips of the longitudinal direction L of the absorbent article 1 are formed in a semicircular shape.

A plurality of second compressing units 13 are also provided spaced apart in the absorber 10 over the entire region excluding the region 11 in which the first compressing units 12 are provided. Herein the plurality of second compressing units 13 may be arranged not only to be spaced apart along the longitudinal direction L of the absorbent article 1, but also to be spaced apart along the width direction W of the absorbent article 1.

Herein, in the plan view shape of the second compressing units 13, as illustrated in FIG. 3, the dimension W2 along the width direction W of the absorbent article 1 is configured so as to be longer than the dimension L2 along the longitudinal direction L of the absorbent article 1.

For example, in terms of the stiffness of the absorber 10, the dimension W2 is preferably 3 mm or less, and the dimension L2 is preferably 2 mm or less.

Also, the plurality of second compressing units 13 are in a shape that comprises a straight line along the width direction W of the absorbent article 1. In this embodiment, in the plurality of second compressing units 13, both tips of the width direction W of the absorbent article 1 are formed in a semicircular shape. It is noted that the plurality of second compressing units 13 may have the same area and shape, or may have different areas and shapes.

According to such a configuration, when an external force from the width direction W of the absorbent article 1 is applied to the absorbent article 1, that is, when an external force from the wearer's inner thighs is applied, then the region 15 corresponding to the excretion unit is not liable to be bent along the longitudinal direction L of the absorbent article 1 due to the second compressing units 13. Accordingly, even when the wearer closes the thighs, it is possible to prevent the region 15 corresponding to the excretion unit from twisting.

Also, according to such a configuration, the region 15 corresponding to the excretion unit is not liable to be bent along the longitudinal direction L of the absorbent article 1 in the rear of the region 15 corresponding to the excretion unit (at the buttocks side) due to the second compressing units 13, and moreover the absorbent article 1 is thus not liable to become wedged in the groove of the buttocks even in situations in which the pressure from wearing shorts is applied along the groove of the buttocks.

Moreover, according to such a configuration, the stiffness of the absorber 10 in the width direction W of the absorbent article 1 can be raised and the absorbent article 1 can be made to be less liable to become wedged in the urethral opening, by means of the second compressing units 13 in the front of the region 15 corresponding to the excretion unit (at the mons pubis side).

Further, according to such a configuration, because the second compressing units 13 are provided spaced apart along the longitudinal direction L of the absorbent article 1, and a plurality of the second compressing units 13 are in a shape that comprises a straight line along the width direction W of the absorbent article 1, high-stiffness units (the second compressing units 13) and low-stiffness units (excluding the second compressing units 13) are alternately repeated, resulting in the presence of a plurality of creases.

As a result, the absorber 10 is easily deformed to match the curvature of the wearer's body and the sensation of the fit of the absorbent article 1 to the wearer's body can be enhanced, because the stiffness of the absorber 10 in the longitudinal direction L of the absorbent article 1 can be lowered.

In particular, even when the absorbent article 1 is repeatedly deformed, the topsheet 21 and the like are not prone to be torn, because in the plurality of second compressing units 13, both tips of the width direction W of the absorbent article 1 are formed in a semicircular shape.

Moreover, according to such a configuration, the absorber 10 is prevented from being easily deformed against an external force from the width direction W of the absorbent article 1 (for example, an external force from the wearer's inner thighs), due to the plurality of second compressing units 13 which are in an elongated shape (W2>L2) in the width direction W of the absorbent article 1.

Also, the dimension W2 along the width direction W of the absorbent article 1 of the second compressing units 13, as illustrated in FIG. 3, may be configured so as to be shorter than an interval a along the width direction W of the absorbent article 1 between adjacent second compressing units 13.

For example, the interval a along the width direction W of the absorbent article 1 between adjacent second compressing units 13 is less than 10 mm, and an interval b along the longitudinal direction L of the absorbent article 1 between adjacent second compressing units 13 is 10 mm or less; more preferably, a and b are both 5 mm or less.

According to such a configuration, the absorbent article 1 is hard but not excessively so, and maintains flexibility and is not easily twisted, such that it is possible to combine a reduction in discomfort (hardness) for the wearer with an improvement in the fit and so on.

Also, as illustrated in FIG. 3, the plurality of first compressing units 12 and the plurality of second compressing units 13 may also each be arranged so as to be staggered.

According to such a configuration, depending on the wearer's movement, when forces F1 and F2 are applied so as to twist the absorber 10, boundary lines L1 and L2 form creases between high-stiffness portions (the first compressing units 12 and the second compressing units 13) and low-stiffness portions (those portions excluding the first compressing units 12 and the second compressing units 13), which are easily bent (that is, easily twisted) such that it is possible to reduce the level of discomfort on the wearer.

Also, the area ratio of the second compressing units 13 in the region 15 corresponding to the excretion unit, as illustrated in FIG. 3, may be configured so as to be lower than the area ratio of the second compressing units 13 in the peripheral region of the region 15 corresponding to the excretion unit.

For example, the number of second compressing units 13 in the region 15 corresponding to the excretion unit may be configured so as to be less than the number of second compressing units 13 in the peripheral region of the region 15 corresponding to the excretion unit.

Also, a row of second compressing units 13 arranged along the longitudinal direction L of the absorbent article 1 may be configured so as to be less in the region 15 corresponding to the excretion unit, whereas a line of second compressing units 13 arranged along the width direction W of the absorbent article 1 may also be configured to be less in the region 15 corresponding to the excretion unit.

In addition, as illustrated in FIG. 4, although the number of second compressing units 13 in the region 15 corresponding to the excretion unit and the number of second compressing units 13 in the peripheral region of the region 15 corresponding to the excretion unit may be the same, the area of the second compressing units 13 in the region 15 corresponding to the excretion unit may be configured so as to be smaller It is noted that by combining some of the patterns described above, the area ratio of second compressing units 13 in the region 15 corresponding to the excretion unit may be configured so as to be less than the area ratio of the second compressing units 13 in the peripheral region of the region 15 corresponding to the excretion unit.

EXAMPLE

Herein, the area ratio of the second compressing units 13 in the region 15 corresponding to the excretion unit is calculated by "(the total area of the second compressing units 13 provided within the region 15 corresponding to the excretion unit)÷(the area of the region 15 corresponding to the excretion unit)", and the area ratio of the second compressing units 13 in the peripheral region of the region 15 corresponding to the excretion unit is calculated by "(the total area of the second compressing units 13 provided within the peripheral region of the region 15 corresponding to the excretion unit)÷(the area of the peripheral region of the region 15 corresponding to the excretion unit)".

It is noted that as a method of measuring the area ratios of the second compressing units 13, for example, the area ratio of the second compressing units 13 within a prescribed range centered on a specific point in the second compressing units 13 (for example, a size range of 2 cm×2 cm) may be measured.

Herein, for example, the area ratio of the second compressing units 13 in the region 15 corresponding to the excretion unit and the area ratio of the second compressing units 13 in the peripheral region of the region 15 corresponding to the excretion unit are both 10% or less, or more preferably 5% or less.

Also, as illustrated in FIG. 5, the area ratios of the second compressing units 13 may be configured so as to be higher in proportion approaching the region 15 corresponding to the excretion unit in the longitudinal direction L of the absorbent article 1.

According to such a configuration, the stiffnesses of the region 15 corresponding to the excretion unit and the peripheral region of the region 15 corresponding to the excretion unit are higher than the stiffness of the regions on the exterior thereof, and thus it is possible to prevent the region 15 corresponding to the excretion unit from being easily deformed.

Also, according to such a configuration, the area ratios of the second compressing units 13 are configured so as to be higher in proportion approaching the region 15 corresponding to the excretion unit in the longitudinal direction L of the absorbent article 1, and it is more liable to bend along the width direction W of the absorbent article 1 at the position corresponding to the portions of the wearer's buttocks that have high curvature (namely, in the front and rear of the region 15 corresponding to the excretion unit). Accordingly, it is possible to enhance the fit for the wearer.

According to such a configuration, in the region 15 corresponding to the excretion unit, because a region 16 is provided in which the weight per unit area of the absorber 10 is higher than in the peripheral region, and because the area ratio of the second compressing units 13 therein is lower than the area ratio of the second compressing units 13 in the peripheral region thereof, it is possible to raise the fluid-absorption performance in the region 15 corresponding to the excretion unit, and moreover it is possible to prevent the wearer from experiencing the sensation of a foreign body even after fluid has been absorbed.

Also, as illustrated in FIG. 3, the size of the plan view shape in the region 16 in which the weight per unit area of the absorber 10 is higher than that in the peripheral region is configured so as to be smaller than the size of the plan view shape in the region 15 corresponding to the excretion unit. That is, the dimensions for the longitudinal direction L and the width direction W of the absorbent article 1 in the region 16 are configured so as to be smaller than the dimension for the longitudinal direction L and the width direction W of the absorbent article 1 in the region 15 corresponding to the excretion unit.

For example, in terms of the stiffness of the absorber 10, the dimensions of the longitudinal direction L and the dimensions of the width direction W of the absorbent article 1 in the region 15 corresponding to the excretion unit are longer than those in the region 16 by 1 mm or more; more preferably, by 5 mm or more.

Also, as illustrated in FIG. 3, at least one of the second compressing units 13 may be arranged so as to straddle a boundary X between the region 16 in which the weight per unit area of the absorber 10 is higher and a region in which the weight per unit area of the absorber 10 is lower.

According to such a configuration, when an external force from the width direction W of the absorbent article 1 is applied to the absorbent article 1, that is, when an external force from the wearer's inner thighs is applied, it is possible to prevent from bending at the boundary X described above, and to reliably facilitate bending along the longitudinal direction L of the absorbent article 1 due to the plurality of first compressing units 12.

Herein, in the region 16 in which the weight per unit area of the region is higher, when the same area ratio of second compressing units 13 is applied as that in the peripheral region of the region 15 corresponding to the excretion unit, the stiffness of this region 16 tends to be excessively high, which may give the wearer the sensation of a foreign body.

In particular, in the production line for the absorber 10, as will be described below, because of being configured to produce the absorber 10 and then form the second compressing units 13 thereon, when the production line of the absorber 10 crawls in a direction CD, then the likelihood of this problem occurring increases.

Accordingly, as described above, an excessive increase in stiffness in the region 16 is avoided by making the region 16 narrower than the region 15 corresponding to the excretion unit, and even when the production line of the absorber 10 crawls in the direction CD, it is possible to prevent the occurrence of excessive difference in stiffness between the left and right within the region 15 corresponding to the excretion unit.

Also, the stiffness in the front of the longitudinal direction L of the absorbent article 1 may be configured to as to be greater than the stiffness in the rear of the longitudinal direction L of the absorbent article 1.

For example, in an absorbent article 1 in which the dimension of the longitudinal direction L is 27 cm or more (such as a night napkin), a leakage-preventing unit for preventing leakage is often provided, but when the stiffness in the front of the longitudinal direction L of the absorbent article 1 is lowered, the front of the longitudinal direction L of the absorbent article 1 tends to bend back with stress of the elastic member provided on the leakage-preventing unit, which may end up giving discomfort to the wearer.

Accordingly, in order to avoid such a situation, as described above, the stiffness in the front of the longitudinal direction L of the absorbent article 1 may be made to be greater than the stiffness in the rear of the longitudinal direction L of the absorbent article 1.

Also, the stiffness in the rear of the longitudinal direction L of the absorbent article 1 may be configured so as to be greater than the stiffness in the front of the longitudinal direction L of the absorbent article 1.

For example, in an absorbent article 1 in which the dimension of the longitudinal direction L is less than 27 cm (such as daytime napkins or regular-type napkins), when the stiffness in the rear of the longitudinal direction L of the absorbent article 1 is reduced, the absorbent article may become excessively wedged in the groove of the buttocks in the area around the wearer's anus, giving the wearer the sensation of a foreign body.

Accordingly, in order to avoid such a situation, as described above, the stiffness in the rear of the longitudinal direction L of the absorbent article 1 may be made to be greater than the stiffness in the front of the longitudinal direction L of the absorbent article 1.

Herein the stiffness in the front (or rear) of the longitudinal direction L of the absorbent article 1 may be increased by increasing the weight per unit area of the absorber 10, and the stiffness in the front (or rear) of the longitudinal direction L of the absorbent article 1 may be increased by forming compressing units.

For example, as illustrated in FIG. 3, the stiffness in the front (or rear) of the longitudinal direction L of the absorbent article 1 may be configured to as to be greater than the stiffness in the rear (or front) of the longitudinal direction L of the absorbent article 1 by forming compressing units 50 on both-side edges in the front (or rear) of the longitudinal direction L of the absorbent article 1.

Subsequently, an explanation is provided for a part of the method for producing the absorbent article 1 according to this embodiment with reference to FIG. 6 and FIG. 7, specifically, for a part of the method for producing the absorber 10 of the absorbent article 1 according to this embodiment. It is noted that for the method not recited in FIG. 6 and FIG. 7, an existing method can be used.

As illustrated in FIG. 6, in step S101, the absorber core 10A, which includes a lamination of ground pulp and absorbent polymer, is wrapped by core wrap 10B so as to perforate pressure rollers 100A and 100A-1.

In step S102, an absorber cutter 100B is used to produce the absorber 10 by cutting to a prescribed dimension and shape.

In step S103, the absorber 10, which is produced by means of the absorber cutter 100B, is conveyed by means of conveyor belt 100C.

Herein, because a space is found between the absorber cutter 100B and the conveyor belt 100C, as illustrated in FIG. 7, the absorber 100 tends to dangle in a vertical direction A from its own weight immediately after being produced by means of the absorber cutter 100B.

In order to resolve this problem, it is necessary to increase the stiffness of the absorber 10. Herein, by increasing the overall stiffness of the absorber 10, the wearer tends to experience the sensation of a foreign body, and therefore the stiffness of the absorber 10 increases only in the front of a direction MD.

That is, in an absorbent article 1 in which the dimension of the longitudinal direction L is 27 cm or more (such as a night napkin), in order to arrange the front of the longitudinal direction L of the absorbent article 1 in the front of the direction MD, the stiffness in the front of the longitudinal direction L of the absorbent article 1 is increased.

On the other hand, in an absorbent article 1 in which the dimension of the longitudinal direction L is less than 26 cm (such as daytime napkins or regular-type napkins), the stiffness in the rear of the longitudinal direction L of the absorbent article 1 is increased in order to arrange the rear of the longitudinal direction L of the absorbent article 1 in the front of the direction MD.

Herein, for example, the stiffness of the absorber 10 is increased only in a region that is 50% or less in the front of the absorber 10, more preferably in a region that is 30% or less in the front of the absorber 10.

According to such a configuration, it is possible to improve the straight-line stability in the production line of the absorber 10.

Thus, the present invention has been explained in detail by using the above-described embodiments; however, it is obvious that for persons skilled in the art, the present invention is not limited to the embodiments explained herein. The present invention can be implemented as a corrected and modified mode without departing from the gist and the scope of the present invention defined by the claims. Therefore, the description of the specification is intended for explaining the example only and does not impose any limited meaning to the present invention.

The entire contents of Japanese Patent Application No. 2010-174040 (filed on Aug. 2, 2010) are incorporated in the present specification by reference.

INDUSTRIAL APPLICABILITY

According to aspects of the present invention, provided is an absorbent article in which it is possible to maintain flexibility and prevent twisting while providing a product that is entirely thin

EXPLANATIONS OF NUMERALS

1 . . . absorbent article
10 . . . absorber
12 . . . first compressing unit
13 . . . second compressing unit
15 . . . region corresponding to the excretion unit
21 . . . topsheet
22 . . . backsheet
30 . . . wing unit
31 . . . side sheet

The invention claimed is:

1. An absorbent article comprising:
a liquid-permeable topsheet;
a liquid-impermeable backsheet; and
an absorber disposed between the topsheet and the backsheet, wherein
a plurality of first compressing units are provided spaced apart on both-side edges of a region corresponding to an excretion unit in the absorber, a plurality of second compressing units are provided spaced apart over the entire region in the absorber excluding the region in which the first compressing units are provided, the dimensions along the longitudinal direction of the absorbent article in the plan view shape of the first compressing units are configured so as to be longer than the dimensions along the width direction of the absorbent article, and the dimensions along the width direction of the absorbent article in the plan view shape of the second compressing units are configured so as to be longer than the dimensions along the longitudinal direction of the absorbent article, wherein an area ratio of the second compressing units in the region corresponding to the excretion unit is configured so as to be lower than an area ratio of the second compressing units in a peripheral region of the region corresponding to the excretion unit, and in the region corresponding to the excretion unit, a region in which the weight per unit area of the absorber is configured so as to be higher than in the peripheral region is provided.

2. The absorbent article according to claim 1, wherein
the first compressing units are provided spaced apart along the longitudinal direction of the absorbent article, and
the second compressing units are provided spaced apart along the width direction of the absorbent article.

3. The absorbent article according to claim 2, wherein
the stiffness in the front of the longitudinal direction of the absorbent article is configured to as to be greater than the stiffness in the rear of the longitudinal direction of the absorbent article.

4. The absorbent article according to claim 2, wherein
the stiffness in the rear of the longitudinal direction of the absorbent article is configured to as to be greater than the stiffness in the front of the longitudinal direction of the absorbent article.

5. The absorbent article according to claim 2, wherein
the area ratios of the second compressing units are configured so as to be higher in proportion approaching the region corresponding to the excretion unit in the longitudinal direction of the absorbent article.

6. The absorbent article according to claim 2, wherein
at least one of the second compressing units is arranged so as to straddle a boundary between the region in which the weight per unit area of the absorber is higher and a region in which the weight per unit area of the absorber is lower.

7. The absorbent article according to claim 2, wherein
the dimension along the width direction of the absorbent article of the second compressing units is configured so as to be shorter than an interval along the width direction W of the absorbent article between adjacent second compressing units.

8. The absorbent article according to claim 7, wherein the plurality of first compressing units and the plurality of second compressing units are each arranged so as to be staggered.

9. The absorbent article according to claim 2, wherein the plurality of first compressing units and the plurality of second compressing units are in a shape that comprises a straight line.

10. The absorbent article according to claim 1, wherein
the stiffness in the front of the longitudinal direction of the absorbent article is configured to as to be greater than the stiffness in the rear of the longitudinal direction of the absorbent article.

11. The absorbent article according to claim 1, wherein
the stiffness in the rear of the longitudinal direction of the absorbent article is configured to as to be greater than the stiffness in the front of the longitudinal direction of the absorbent article.

12. The absorbent article according to claim 1, wherein
the area ratios of the second compressing units are configured so as to be higher in proportion approaching the region corresponding to the excretion unit in the longitudinal direction of the absorbent article.

13. The absorbent article according to claim 1 wherein
at least one of the second compressing units is arranged so as to straddle a boundary between the region in which the weight per unit area of the absorber is higher and a region in which the weight per unit area of the absorber is lower.

14. The absorbent article according to claim 1, wherein
the dimension along the width direction of the absorbent article of the second compressing units is configured so as to be shorter than an interval along the width direction W of the absorbent article between adjacent second compressing units.

15. The absorbent article according to claim 14, wherein the plurality of first compressing units and the plurality of second compressing units are each arranged so as to be staggered.

16. The absorbent article according to claim 1, wherein the plurality of first compressing units and the plurality of second compressing units are in a shape that comprises a straight line.

* * * * *